(12) United States Patent
Sordillo

(10) Patent No.: US 7,160,696 B2
(45) Date of Patent: Jan. 9, 2007

(54) BOVINE LYMPHOCYTE-DERIVED ANTIBACTERIAL PROTEIN

(75) Inventor: Lorraine Sordillo, Port Matilda, PA (US)

(73) Assignee: The Penn State Research Foundation, University Park, PA (US)

( * ) Notice: Subject to any disclaimer, the term of this patent is extended or adjusted under 35 U.S.C. 154(b) by 475 days.

(21) Appl. No.: 10/413,600

(22) Filed: Apr. 14, 2003

(65) Prior Publication Data

US 2004/0204575 A1    Oct. 14, 2004

(51) Int. Cl.
*C12N 15/00* (2006.01)
*C12N 5/00* (2006.01)
*C07H 21/00* (2006.01)

(52) U.S. Cl. .................. 435/69.1; 435/325; 435/320.1; 536/23.1

(58) Field of Classification Search .................. None
See application file for complete search history.

(56) References Cited

U.S. PATENT DOCUMENTS 6,011,012 A * 1/2000 Ni et al. .................. 514/12

FOREIGN PATENT DOCUMENTS

WO    WO 98/08534    3/1998

OTHER PUBLICATIONS

Lewis et al. Subracted Lewin Cattle Spleen ESTs. Accession Number: BM366436. See Appendix A (Jan. 19, 2002).*
Meinkoth et al. Hybridization of of Nucleic Acids Immobilized on Solid Supports. Analytical Biochemistry vol. 138:267-284, (1984).*
Wyckoff III, JH, et al., Comparison of *Brucella abortus* antigen preparations for in vitro stimulation of immune bovine T-lymphocyte cell lines, *Veterinary Immunology and Immunopathology*, vol. 36, pp. 45-64 (1993).
Andersson, M., et al., NK-lysin, a novel effector peptide of cytotoxic T and NK cells. Structure and cDNA cloning of the porcine form, induction by interleukin 2, antibacterial and antitumor activity, *EMBO Journal*, vol. 14, No. 8, pp. 1615-1625 (1995).
Andersson, M., et al., NK-lysin, structure and function of a novel effector molecule of porcine T and NK cells, *Veterinary Immunology and Immunopathology*, vol. 54, pp. 123-126 (1996).
Pena, SV., et al., Processing, subcellular localization, and function of 519 (Granulysin), a human late T cell activation molecule with homology to small, lytic granule proteins, *American Association of Immunologists*, vol. 158, pp. 2680-2688 (1997).
Garcia-Penarrubia, P. et al., Prostaglandins from human T suppressor/cytotoxic cells modulate natural killer antibacterial activity, *Journal of Experimental Medicine*, vol. 170, pp. 601-606 (1989).
Garcia-Penarrubia, P., et al., Antibacterial activity of human natural killer cells, *Journal of Experimental Medicine*, vol. 169, pp. 99-113 (1989).
Levitz, SM, et al., Direct antimicrobial activity of T cells, *Immunology Today*, vol. 16, pp. 387-391 (1995).
Quiroga, GH, et al., Cytologic responses of *Staphylococcus aureus*-infected mammary glands of heifers to interferon gamma and interleukin-2 treatment, *American Journal of Veterinary Research*, vol. 54, No. 11, pp. 1894-1900 (1993).
Louhi-Lehtio, M., et al, Antibacterial Susceptibility of Bovine-mastitis Pathogens tested directely in milk from infected quarters, *J. Vet. Med. I*, 41:101-112 (1994).
Singh, PK, et al., Synergistic and additive killing by antimicrobial factors found in human airway surface liquid, *Am. J. Physiol. Lung Cell Mol. Physiol.*, 279:L799-L805 (2000).
Sable, S., Antibacterial Activity evaluation of Microcin J25 against diarrheagenic *Escherichia coli*, *Applied and Environmental Microbiology*, 66(10):4595-4597 (2000).
Pettit, DK and Gombotz, WR, The development of site-specific drug-delivery systems for protein and peptide biopharmaceuticals, *Tibtechl*, 16:343-349 (1998).
Gaddy, J., and Broxmeyer, HE, Cord Blood CD16+45- cells with low lytic activity are possible precursors of mature natural killer cells, *Cellular Immunology*, 180:132-142 (1997).
Lotzova, E. and Savary, CA, Human natural killer cell development from bone marrow progenitors: analysis of phenotype, cytotoxicity and growth, *Nat. Immun.*, 12:209-217 (1993).

* cited by examiner

*Primary Examiner*—Marianne P. Allen
*Assistant Examiner*—Regina M. DeBerry
(74) *Attorney, Agent, or Firm*—Howard Eisenberg, Esq.

(57) ABSTRACT

A nucleic acid sequence encoding a polypeptide having antibacterial activity, which nucleic acid sequence has the nucleotide sequence of Bases 198 to 452 of Seq. ID No. 13 or is a nucleic acid that hybridizes under highly stringent conditions to a complement of a nucleic acid having the nucleotide sequence of Bases 198 to 452 of Seq. ID No. 13, and the polypeptide encoded thereby.

8 Claims, 7 Drawing Sheets

| Primer Set | Sequence | Annealing temperature | Product size |
| --- | --- | --- | --- |
| Optimal | Forward 5'-GACGGCCCATCTGTGTGATGGAGAC-3'<br>Reverse 5'-TCAGCAGCCTCATCTTGCTGCACAC-3' | 72°C | 215 bp |
| Product #1 | Forward 5'-GGCCCATCTGTGTGATGGAGACGAG-3'<br>Reverse 5'-CGGGCTGATCTCCCAACTTGTCCAT-3' | 72°C | 155 bp |
| Product #2 | Forward 5'-GTGATGGAGACGAGTTGTGCCAGGG-3'<br>Reverse 5'-TCAGCAGCCTCATCTTGCTGCACAC-3' | 72°C | 201 bp |
| Product #4 | Forward 5'-GTGATGGAGACGAGTTGTGCCAGGG-3'<br>Reverse 5'-CGGGCTGATCTCCCAACTTGTCCAT-3' | 72°C | 144 bp |
| Product #5 | Forward 5'-CAGCTGCCTCAACATGACCTCCTGG-3'<br>Reverse 5'-CCCTGGCACAACTCGTCTCCATCAC-3' | 72°C | 147 bp |
| Product #6 | Forward 5'-CAGCTGCCTCAACATGACCTCCTGG-3'<br>Reverse 5'-CGGGCTGATCTCCCAACTTGTCCAT-3' | 72°C | 266 bp |

FIGURE 1

```
TIGR Database Bovine Sequence TC90773 GGGACCCTGCCAGGTGCACAGCGCTCTATAAAACAAGCTGTGGAGGGAGCC
RACE 632 bp putative bSAPLIP Sequence     ---------------------------------------------------

TGGGCAGCTGCCTCAACATGACCTCCTGGGCTGTCCTGCTCATCACCTCGGTGCTCCTGGTTGCCCCAGGGCTGGCTTTTTCCGGTCTG
-----AGCTGCCTTAACATGACCTCCTGGGCTGTCCTGATCATCACCTCGGTGCTCCTGGTTGCCCCAGGGCTGGCTTTTTCCGGTCTG
                  ----------------------     ----------------------------------------------

ACTCCTGAGAGCCACGACCAGGCGACGGCCCATCTGTGTGATGGAGACGAGTTGTGCCAGGGCCTGGCCCTGGAGGATCCCCAGGGTGA
ACTCCTGAGAGCCACGACCAGGCGACGGCCCATCTATGTGATGGAGACGAGTTGTGCCAGGGACTGGCCCTGGAGGATCCCCAGGGTGA
                                   -----                           -----

CCTGCTGCTCCAAGGAGAAGAGCTAAGCCTACGCTGTGGTTCTTGTCGGAGAATAATACAACATCTGATGGACAAGTTGGGAGATCAGA
CCTGCTGCTCCAAGCAGAAGAGCTGAGCCTACGATGTGGTTCTTGTCGGAGAATAATACAACATCTGATGGACAAGTTGGGAGATCAGC
             -         -         -                                                      -

GCGATGAGGTGAGACGGGAGGCTTGTGGGACCTGGCGGGTGGAGAGGTGCCCCCAAGTGGAGTGGGAAGGGCTGGGAATCCTTACCTAG
CCGATGAGAATACCGTTATCGAGGAGGCCTCCAAGGTGTGCAGCAAGATGAGGCTGCTGAAAGGTCTGTGCAACTCAATCATGAAGAAA

GCTTTTTAAATGAGCTGGAAAGTGGGATGTACTTAGCTTTGAGTGAATTCTTAATAAGTGGAGGCATCATCACCAGAACCACAGTTTCA
TTTCTCCGTACCATCGCTGAGGACATCGTAGCTGGAAAAACCTCTCAGGTTATCTGTGTGGACATCAAGATGTGCAAAAGCAAGCCAGT

CTTTCCATCCCTCCCTCTCCTTGGCTCCCCCAACCTACCAGCATCACTACCTTCACCCTGGGGTATTCAGATTTATCCCCTTCCATGGG
AGGTTTCATTTGATTCCCTGGGTCCTCTTACCCCATCCTGGGGAAAAAGCACAGAAACTCCAGTATTCCTTGGCCCGGCTCCCTTCTTC
              -

ACATGTCAGAAGAAGATATTTCAAAAGCAATGGACCAAAGCTCCAAGCTTGGATACCCTCCTAACCCACCACAGCCGCCCCCCACCAGC
CTGAATCCAGGAGTCTTTCTCTCCAGTTTCTGGCACCAAACTCCCTTCACTGCCTTTCCCTCTCAGAATAAAATATTCATGCAAGAAAA

AGATGGAGCCCCCAGTCTGGCCCTGGACCAGAAGCTAGATAGACAGAGCCTTTAAAGTGGGTCTGGGCACCACTCTCCACCCAGAAGAC
AAAAAAAAAAAAAA

AGGGCCTGGGTATACAGAGGCTAAGACTCGGCAGGGTCAATTGTCCTTTCCAGAGCTCCTGCTGGCCAGGCTTGAGATGGGGAGGGGGC
TGAGCCCTGTCTCTCCAGTCCCTGCTCCCACTACCACCTGGCACCAACTCCCGGGACCCAGCGCTCCCACTGCCAGACCCGCTGAGAGCC
CAAGGCTGCCGGGGCCTGCAGAGAGACAGTGCCCAGCAGGGCTCACCTGAGGCCCGTTTCCCACCACGGTGCTGCTGCTGCAGAATACCG
TTATCGAGGAGGCCTCCAAGGTGTGCAGCAAGATGAGGCTGCTGAAAGGTCTGTGCAAGTCAATCATGAAGAAATTTCTCCGTACCATCG
CTGAGGACATCGTAGCTGGAAAAACCTCTCGGGT
```

FIGURE 2

5' RACE-AGCTGCCTTAACATGACCTCCTGGGCTGTCCTGATCATCACCTCGGTGCTCCT
GGTTGCCCCAGGGCTGGCTTTTTCCGGTCTGACTCCTGAGAGCCACGACCAGGCGACGGC
CCATCTATGTGATGGAGACGAGTTGTGCCAGGGACTGGCCCTGGAGGATCCCCAGGGTGA
CCTGCTGCTCCAAGGAGAAGAGCTGAGCCTACGATGTGGTTCTTGTCGGAGAATAATACA

3' RACE-ATGGACAAGTTGGGAGATCAGCCCGATGAGAATACCGTTATCGAGGAGGCCTC
ACATCTGATGGACAAGTTGGGAGATCAGCCCGATGAGAATACCGTTATCGAGGAGGCCTC

CAAGGTGTGCAGCAAGATGAGGCTGCTGAAAGGTCTGTGCAAGTCAATCATGAAGAAATT
CAAGGTGTGCAGCAAGATGAGGCTGC

TCTCCGTACCATCGCTGAGGACATCGTAGCTGGAAAAACCTCTCAGGTTATCTGTGTGGA
CATCAAGATGTGCAAAAGCAAGCCAGTAGGTTTCATTTGATTCCCTGGGTCCTCTTACCC
CATCCTGGGGAAAAAGCACAGAAACTCCAGTATTCCTTGGCCCGGCTCCCTTCTTCCTGA
ATCCAGGAGTCTTCTCTCCAGTTTCTGGCACCAAACTCCCTTCACTGCCTTTCCCTCTCA
GAATAAAATATTCATGCAAGAAAAAAAAAAAAAAAAA

FIGURE 3

```
Put. bSAPLIP  MTSWAVLLITSVLLVAPGLAFSGLTPESHDQATAHLCDGDELCQGLALED
NK-Lysin                       PGLAFSGLTPEHSALARAHPCDGEQFCQNLAPED
Granulysin    MATWALLLLAAMLLGNPGLVFSRLSPEYYDLARAHLRDEEKSCPCLAQEG
                 ===-== =+==       =  ==   = ++ =    == =-

PQGDLLLQGEELSLRCGSCRRIIQHLMDKLGDQPDENTVIEEASKVCSKMR-LLKGLCKSIMK
PQGDQLLQREELGLICESCRKIIQKLEDMVGPQPNEDTVTQAASRVCDKMK-ILRGVCKKIMR
PQGDLLTKTQELGRDYRTCLTIVQKLKKMV-DKPTQRSVSNAATRVCRTGRSRWRDVCRNFMR
==== = + +==-    += =+=+= - +  += + += + =++== - +    +-+= -+=+

KFLRTIAEDIVAGKTSRVICVDIKMCKSKPVGFI
TFLRRISKDILTGKKPQAICVDIKICKEK-TGLI
RYQSRVTQGLVAGETAQQICEDLRLCIPS-TGPL
 +   +++-+++=  --+ ==  +++=   - -= +
```

FIGURE 4

```
Put. bSAPLIP  PGLAFSGLTPESHDQATAHLCDGDELCQGLALEDPQGDLLQGEEL-SLRC
                                                          ^

NK-Lysin      PGLAFSGLTPEHSALARAHPCDGEQFCQNLAPEDPQGDQLLQREEL-GLIC
                                                          ^ granulysin    PGLVFSRLSPEYYDLARAHLRDEEKSCPCLAQEGPQGDLLTKTQEL-GRDY
                                                          ^

GSCRRIIQHLMDKLGDQPDENTVIEEASKVCSKMR-LLKGLCKSIMKKFLRTIAEDIVAGKT

ESCRKIIQKLEDMVGPQPNEDTVTQAASRVCDKMK-ILRGVCKKIMRTFLRRISKDILTGKK

RTCLTIVQKLKKMV-DKPTQRSVSNAATRVCRTGRSRWRDVCRNFMRRYQSRVTCGLVAGET

SRVICVDIKMCKSKPVGFI

PQAICVDIKICKEK-TGLI

AQQICEDLRLCIPS-TGPL
```

FIGURE 5

```
putative
bSAPLIP    SLRCGSCRRIIQHLMDKLGDQPDENTVIEEASKVCSKMR-LLKGLCKSIMKKFLRTIAEDIVAGKTSRVICVDIKMCKSKPVGFI
            1 2                              3                   4                    5      6

NK-lysin   GLICESCRKIIQKLEDMVGPQPNEDTVTQAASRVCDKMK-ILRGVCKKIMRTFLRRISKDILTGKKPQAICVDIKICKEK-TGLI
            1 2                              3                   4                    5  6 granulysin GRDYRTCLTIVQKLKKMV-DKPTQRSVSNAATRVCRTGRSRWRDVCRNFMRRYQSRVTQGLVAGETAQQICEDLRLCIPS-TGPL
            1 2                              3                   4                   5  6
                                                                                          ^
```

FIGURE 6

```
putative
bSAPLIP     SLRCGSCRRIIQHEMDKLIGDQRDENTMIEEASKVCSKMR-LEKGICKSEMKKFLRTHAEDIVAGKTSRVICVDRMCKSKPVGFI NK-lysin    GLICESCRKIIQKLEDMVGPQPNEDTVTQAASRVCDKMK-TERGVCKKIMRTELRRISKDIITGKKPQAICVDIKICKEK-TGLI granulysin  GRDYRTCLTIVQKLKKMV-DKPTQRSVSNAATRVCRTGRSRWRDVCRNFMRRYQSRVTQGLVAGETAQQICEDIRLCIPS-TGPI
                                                                                            ʌ
```

FIGURE 7

SEQUENCE LISTING

<160> NUMBER OF SEQ ID NOS: 30

<210> SEQ ID NO 1
<211> LENGTH: 25
<212> TYPE: DNA
<213> ORGANISM: Artificial
<220> FEATURE:
<223> OTHER INFORMATION: Primer sequence

<400> SEQUENCE: 1
gacggcccat ctgtgtgatg gagac                                         25

<210> SEQ ID NO 2
<211> LENGTH: 25
<212> TYPE: DNA
<213> ORGANISM: artificial
<220> FEATURE:
<223> OTHER INFORMATION: Primer sequence

<400> SEQUENCE: 2
tcagcagcct catcttgctg cacac                                         25

<210> SEQ ID NO 3
<211> LENGTH: 25
<212> TYPE: DNA
<213> ORGANISM: artificial
<220> FEATURE:
<223> OTHER INFORMATION: Primer sequence

<400> SEQUENCE: 3
ggcccatctg tgtgatggag acgag                                         25

<210> SEQ ID NO 4
<211> LENGTH: 25

```
<212> TYPE: DNA
<213> ORGANISM: artificial
<220> FEATURE:
<223> OTHER INFORMATION: Primer sequence

<400> SEQUENCE: 4
cgggctgatc tcccaacttg tccat                                   25

<210> SEQ ID NO 5
<211> LENGTH: 25
<212> TYPE: DNA
<213> ORGANISM: artificial
<220> FEATURE:
<223> OTHER INFORMATION: Primer sequence

<400> SEQUENCE: 5
gtgatggaga cgagttgtgc caggg                                   25

<210> SEQ ID NO 6
<211> LENGTH: 25
<212> TYPE: DNA
<213> ORGANISM: Artificial
<220> FEATURE:
<223> OTHER INFORMATION: Primer sesquence

<400> SEQUENCE: 6
tcagcagcct catcttgctg cacac                                   25

<210> SEQ ID NO 7
<211> LENGTH: 25
<212> TYPE: DNA
<213> ORGANISM: Artificial
<220> FEATURE:
<223> OTHER INFORMATION: primer sequence

<400> SEQUENCE: 7
gtgatggaga cgagttgtgc caggg                                   25

<210> SEQ ID NO 8
<211> LENGTH: 25
<212> TYPE: DNA
<213> ORGANISM: Artificial
<220> FEATURE:
<223> OTHER INFORMATION: Primer sequence

<400> SEQUENCE: 8
cgggctgatc tcccaacttg tccat                                   25

<210> SEQ ID NO 9
<211> LENGTH: 25
<212> TYPE: DNA
<213> ORGANISM: artificial
<220> FEATURE:
<223> OTHER INFORMATION: Primer sequence

<400> SEQUENCE: 9
cagctgcctc aacatgacct cctgg                                   25

<210> SEQ ID NO 10
<211> LENGTH: 25
<212> TYPE: DNA
<213> ORGANISM: Artificial
<220> FEATURE:
<223> OTHER INFORMATION: Primer Sequence

<400> SEQUENCE: 10
```

```
ccctggcaca actcgtctcc atcac                                           25
```

<210> SEQ ID NO 11
<211> LENGTH: 25
<212> TYPE: DNA
<213> ORGANISM: Artificial
<220> FEATURE:
<223> OTHER INFORMATION: Primer Sequence

<400> SEQUENCE: 11

```
cagctgcctc aacatgacct cctgg                                           25
```

<210> SEQ ID NO 12
<211> LENGTH: 25
<212> TYPE: DNA
<213> ORGANISM: Artificial
<220> FEATURE:
<223> OTHER INFORMATION: Primer Sequence

<400> SEQUENCE: 12

```
cgggctgatc tcccaacttg tccat                                           25
```

<210> SEQ ID NO 13
<211> LENGTH: 632
<212> TYPE: DNA
<213> ORGANISM: Bos taurus

<400> SEQUENCE: 13

```
agctgcctta acatgacctc ctgggctgtc ctgatcatca cctcggtgct cctggttgcc     60
ccagggctgg cttttccgg tctgactcct gagagccacg accaggcgac ggcccatcta    120
tgtgatggag acgagttgtg ccagggactg ccctgagg atccccaggg tgacctgctg     180
ctccaaggag aagagctgag cctacgctgt ggttcttgtc ggagaataat acaacatctg    240
atggacaagt tgggagatca gcccgatgag aataccgtta tcgaggaggc ctccaaggtg    300
tgcagcaaga tgaggctgct gaaaggtctg tgcaagtcaa tcatgaagaa atttctccgt    360
accatcgctg aggacatcgt agctggaaaa acctctcagg ttatctgtgt ggacatcaag    420
atgtgcaaaa gcaagccagt aggtttcatt tgattccctg ggtcctctta ccccatcctg    480
gggaaaaagc acagaaactc cagtattcct tggcccggct cccttcttcc tgaatccagg    540
agtcttctct ccagtttctg gcaccaaact cccttcactg cctttccctc tcagaataaa    600
atattcatgc aagaaaaaaa aaaaaaaaa aa                                   632
```

<210> SEQ ID NO 14
<211> LENGTH: 1157
<212> TYPE: DNA
<213> ORGANISM: Bos taurus

<400> SEQUENCE: 14

```
gggaccctgc caggtgcaca gcgctctata aacaagctg tggagggagc ctgggcagct     60
gcctcaacat gacctcctgg gctgtcctgc tcatcacctc ggtgctcctg gttgccccag    120
ggctggcttt ttccggtctg actcctgaga gccacgacca ggcgacggcc catctgtgtg    180
atggagacga gttgtgccag ggcctggccc tgaggatcc ccaggtgac ctgctgctcc     240
aaggagaaga gctaagccta cgctgtggtt cttgtcggag aataatacaa catctgatgg    300
acaagttggg agatcagagc gatgaggtga acgggaggc ttgtgggacc tggcgggtgg    360
agaggtgccc ccaagtggag tgggaagggc tgggaatcct tacctaggct ttttaaatga    420
gctggaaagt gggatgtact tagctttgag tgaattctta ataagtggag gcatcatcac    480
```

```
cagaaccaca gtttcacttt ccatccctcc ctctccttgg ctcccccaac ctaccagcat      540
cactaccttc accctggggt attcagattt atcccctccc atgggagatg tcagaagaag      600
atatttcaaa agcaatggac caaagctcca agcttggata ccctcctaac ccaccacagc      660 cgcccccac cagcagatgg agcccccagt ctggccctgg accagaagct agatagacag       720
agcctttaaa gtgggtctgg gcaccactct ccacccagaa gacagggcct gggtatacag      780
aggctaagac tcggcagggt caattgtcct ttccagagct cctgctggcc aggcttgaga      840
tggggagggg ggctgagccc tgtctctcca gtccctgctc ccactaccac ctggcaccaa      900
ctcccgggac ccagcgctcc cactgccaga cccgctgaga gcccaaggct gccggggcct      960
gcagagagac agtgcccagc agggctcacc tgaggcccgt ttccaccac ggtgctgctg      1020 ctgcagaata ccgttatcga ggaggcctcc aaggtgtgca gcaagatgag ctgctgaaa     1080 ggtctgtgca agtcaatcat gaagaaattt ctccgtacca tcgctgagga catcgtagct     1140
ggaaaaacct ctcgggt                                                    1157
```

<210> SEQ ID NO 15
<211> LENGTH: 319
<212> TYPE: DNA
<213> ORGANISM: Bos taurus

<400> SEQUENCE: 15

```
agctgcctta acatgacctc ctgggctgtc ctgatcatca cctcggtgct cctggttgcc       60
ccagggctgg cttttccgg tctgactcct gagagccacg accaggcgac ggcccatcta      120
tgtgatggag acgagttgtg ccagggactg gccctggagg atccccaggg tgacctgctg      180
ctccaaggag aagagctgag cctacgatgt ggttcttgtc ggagaataat acaacatctg      240
atggacaagt tgggagatca gcccgatgag aataccgtta tcgaggaggc ctccaaggtg      300
tgcagcaaga tgaggctgc                                                   319
```

<210> SEQ ID NO 16
<211> LENGTH: 392
<212> TYPE: DNA
<213> ORGANISM: Bos taurus

<400> SEQUENCE: 16

```
atggacaagt tgggagatca gcccgatgag aataccgtta tcgaggaggc ctccaaggtg       60
tgcagcaaga tgaggctgct gaaaggtctg tgcaagtcaa tcatgaagaa atttctccgt      120
accatcgctg aggacatcgt agctggaaaa acctctcagg ttatctgtgt ggacatcaag      180
atgtgcaaaa gcaagccagt aggtttcatt tgattccctg gtcctctta ccccatcctg       240 gggaaaaagc acagaaactc cagtattcct tggcccggct cccttcttcc tgaatccagg      300
agtcttctct ccagtttctg gcaccaaact cccttcactg cctttccctc tcagaataaa     360
atattcatgc aagaaaaaaa aaaaaaaaa aa                                     392
```

<210> SEQ ID NO 17
<211> LENGTH: 146
<212> TYPE: PRT
<213> ORGANISM: Bos taurus

<400> SEQUENCE: 17

```
Met Thr Ser Trp Ala Val Leu Leu Ile Thr Ser Val Leu Leu Val Ala
1               5                   10                  15

Pro Gly Leu Ala Phe Ser Gly Leu Thr Pro Glu Ser His Asp Gln Ala
```

-continued

```
                    20                  25                  30

Thr Ala His Leu Cys Asp Gly Asp Glu Leu Cys Gln Gly Leu Ala Leu
         35                  40                  45

Glu Asp Pro Gln Gly Asp Leu Leu Gln Gly Glu Leu Ser Leu
 50                  55                  60

Arg Cys Gly Ser Cys Arg Arg Ile Ile Gln His Leu Met Asp Lys Leu
 65                  70                  75                  80

Gly Asp Gln Pro Asp Glu Asn Thr Val Ile Glu Ala Ser Lys Val
                 85                  90                  95

Cys Ser Lys Met Arg Leu Leu Lys Gly Leu Cys Lys Ser Ile Met Lys
                100                 105                 110

Lys Phe Leu Arg Thr Ile Ala Glu Asp Ile Val Ala Gly Lys Thr Ser
             115                 120                 125

Arg Val Ile Cys Val Asp Ile Lys Met Cys Lys Ser Lys Pro Val Gly
         130                 135                 140

Phe Ile
145

<210> SEQ ID NO 18
<211> LENGTH: 129
<212> TYPE: PRT
<213> ORGANISM: Sus scrofa

<400> SEQUENCE: 18

Pro Gly Leu Ala Phe Ser Gly Leu Thr Pro Glu His Ser Ala Leu Ala
 1               5                  10                  15

Arg Ala His Pro Cys Asp Gly Glu Gln Phe Cys Gln Asn Leu Ala Pro
                 20                  25                  30

Glu Asp Pro Gln Gly Asp Gln Leu Leu Gln Arg Glu Leu Gly Leu
             35                  40                  45

Ile Cys Glu Ser Cys Arg Lys Ile Ile Gln Lys Leu Glu Asp Met Val
 50                  55                  60

Gly Pro Gln Pro Asn Glu Asp Thr Val Thr Gln Ala Ala Ser Arg Val
 65                  70                  75                  80

Cys Asp Lys Met Lys Ile Leu Arg Gly Val Cys Lys Lys Ile Met Arg
                 85                  90                  95

Thr Phe Leu Arg Arg Ile Ser Lys Asp Ile Leu Thr Gly Lys Lys Pro
                100                 105                 110

Gln Ala Ile Cys Val Asp Ile Lys Ile Cys Lys Glu Lys Thr Gly Leu
             115                 120                 125

Ile

<210> SEQ ID NO 19
<211> LENGTH: 145
<212> TYPE: PRT
<213> ORGANISM: Homo sapiens

<400> SEQUENCE: 19

Met Ala Thr Trp Ala Leu Leu Leu Leu Ala Ala Met Leu Leu Gly Asn
 1               5                  10                  15

Pro Gly Leu Val Phe Ser Arg Leu Ser Pro Glu Tyr Tyr Asp Leu Ala
                 20                  25                  30

Arg Ala His Leu Arg Asp Glu Glu Lys Ser Cys Pro Cys Leu Ala Gln
             35                  40                  45

Glu Gly Pro Gln Gly Asp Leu Leu Thr Lys Thr Gln Glu Leu Gly Arg
 50                  55                  60
```

```
Asp Tyr Arg Thr Cys Leu Thr Ile Val Gln Lys Leu Lys Lys Met Val
 65                  70                  75                  80

Asp Lys Pro Thr Gln Arg Ser Val Ser Asn Ala Ala Thr Arg Val Cys
                 85                  90                  95

Arg Thr Gly Arg Ser Arg Trp Arg Asp Val Cys Arg Asn Phe Met Arg
            100                 105                 110

Arg Tyr Gln Ser Arg Val Thr Gln Gly Leu Val Ala Gly Glu Thr Ala
        115                 120                 125

Gln Gln Ile Cys Glu Asp Leu Arg Leu Cys Ile Pro Ser Thr Gly Pro
    130                 135                 140

Leu
145

<210> SEQ ID NO 20
<211> LENGTH: 130
<212> TYPE: PRT
<213> ORGANISM: Bos taurus

<400> SEQUENCE: 20

Pro Gly Leu Ala Phe Ser Gly Leu Thr Pro Glu Ser His Asp Gln Ala
 1               5                  10                  15

Thr Ala His Leu Cys Asp Gly Asp Glu Leu Cys Gln Gly Leu Ala Leu
                20                  25                  30

Glu Asp Pro Gln Gly Asp Leu Leu Gln Gly Glu Glu Leu Ser Leu
             35                  40                  45

Arg Cys Gly Ser Cys Arg Arg Ile Ile Gln His Leu Met Asp Lys Leu
     50                  55                  60

Gly Asp Gln Pro Asp Glu Asn Thr Val Ile Glu Ala Ser Lys Val
 65                  70                  75                  80

Cys Ser Lys Met Arg Leu Leu Lys Gly Leu Cys Lys Ser Ile Met Lys
                 85                  90                  95

Lys Phe Leu Arg Thr Ile Ala Glu Asp Ile Val Ala Gly Lys Thr Ser
            100                 105                 110

Arg Val Ile Cys Val Asp Ile Lys Met Cys Lys Ser Lys Pro Val Gly
        115                 120                 125

Phe Ile
    130

<210> SEQ ID NO 21
<211> LENGTH: 129
<212> TYPE: PRT
<213> ORGANISM: Sus scrofa

<400> SEQUENCE: 21

Pro Gly Leu Ala Phe Ser Gly Leu Thr Pro Glu His Ser Ala Leu Ala
 1               5                  10                  15

Arg Ala His Pro Cys Asp Gly Glu Gln Phe Cys Gln Asn Leu Ala Pro
                20                  25                  30

Glu Asp Pro Gln Gly Asp Gln Leu Leu Gln Arg Glu Glu Leu Gly Leu
             35                  40                  45

Ile Cys Glu Ser Cys Arg Lys Ile Ile Gln Lys Leu Glu Asp Met Val
     50                  55                  60

Gly Pro Gln Pro Asn Glu Asp Thr Val Thr Gln Ala Ala Ser Arg Val
 65                  70                  75                  80

Cys Asp Lys Met Lys Ile Leu Arg Gly Val Cys Lys Lys Ile Met Arg
                 85                  90                  95
```

```
Thr Phe Leu Arg Arg Ile Ser Lys Asp Ile Leu Thr Gly Lys Lys Pro
            100                 105                 110

Gln Ala Ile Cys Val Asp Ile Lys Ile Cys Lys Glu Lys Thr Gly Leu
        115                 120                 125

Ile

<210> SEQ ID NO 22
<211> LENGTH: 129
<212> TYPE: PRT
<213> ORGANISM: Homo sapiens

<400> SEQUENCE: 22

Pro Gly Leu Val Phe Ser Arg Leu Ser Pro Glu Tyr Tyr Asp Leu Ala
1               5                   10                  15

Arg Ala His Leu Arg Asp Glu Glu Lys Ser Cys Pro Cys Leu Ala Gln
            20                  25                  30

Glu Gly Pro Gln Gly Asp Leu Leu Thr Lys Thr Gln Glu Leu Gly Arg
        35                  40                  45

Asp Tyr Arg Thr Cys Leu Thr Ile Val Gln Lys Leu Lys Lys Met Val
    50                  55                  60

Asp Lys Pro Thr Gln Arg Ser Val Ser Asn Ala Ala Thr Arg Val Cys
65                  70                  75                  80

Arg Thr Gly Arg Ser Arg Trp Arg Asp Val Cys Arg Asn Phe Met Arg
                85                  90                  95

Arg Tyr Gln Ser Arg Val Thr Gln Gly Leu Val Ala Gly Glu Thr Ala
            100                 105                 110

Gln Gln Ile Cys Glu Asp Leu Arg Leu Cys Ile Pro Ser Thr Gly Pro
        115                 120                 125

Leu

<210> SEQ ID NO 23
<211> LENGTH: 84
<212> TYPE: PRT
<213> ORGANISM: Bos taurus

<400> SEQUENCE: 23

Ser Leu Arg Cys Gly Ser Cys Arg Arg Ile Ile Gln His Leu Met Asp
1               5                   10                  15

Lys Leu Gly Asp Gln Pro Asp Glu Asn Thr Val Ile Glu Glu Ala Ser
            20                  25                  30

Lys Val Cys Ser Lys Met Arg Leu Leu Lys Gly Leu Cys Lys Ser Ile
        35                  40                  45

Met Lys Lys Phe Leu Arg Thr Ile Ala Glu Asp Ile Val Ala Gly Lys
    50                  55                  60

Thr Ser Arg Val Ile Cys Val Asp Ile Lys Met Cys Lys Ser Lys Pro
65                  70                  75                  80

Val Gly Phe Ile

<210> SEQ ID NO 24
<211> LENGTH: 83
<212> TYPE: PRT
<213> ORGANISM: Sus scrofa

<400> SEQUENCE: 24

Gly Leu Ile Cys Glu Ser Cys Arg Lys Ile Ile Gln Lys Leu Glu Asp
1               5                   10                  15
```

Met Val Gly Pro Gln Pro Asn Glu Asp Thr Val Thr Gln Ala Ala Ser
            20                  25                  30

Arg Val Cys Asp Lys Met Lys Ile Leu Arg Gly Val Cys Lys Lys Ile
        35                  40                  45

Met Arg Thr Phe Leu Arg Arg Ile Ser Lys Asp Ile Leu Thr Gly Lys
    50                  55                  60

Lys Pro Gln Ala Ile Cys Val Asp Ile Lys Ile Cys Lys Glu Lys Thr
65                  70                  75                  80

Gly Leu Ile

<210> SEQ ID NO 25
<211> LENGTH: 83
<212> TYPE: PRT
<213> ORGANISM: Homo sapiens

<400> SEQUENCE: 25

Gly Arg Asp Tyr Arg Thr Cys Leu Thr Ile Val Gln Lys Leu Lys Lys
1               5                  10                  15

Met Val Asp Lys Pro Thr Gln Arg Ser Val Ser Asn Ala Ala Thr Arg
            20                  25                  30

Val Cys Arg Thr Gly Arg Ser Arg Trp Arg Asp Val Cys Arg Asn Phe
        35                  40                  45

Met Arg Arg Tyr Gln Ser Arg Val Thr Gln Gly Leu Val Ala Gly Glu
    50                  55                  60

Thr Ala Gln Gln Ile Cys Glu Asp Leu Arg Leu Cys Ile Pro Ser Thr
65                  70                  75                  80

Gly Pro Leu

<210> SEQ ID NO 26
<211> LENGTH: 32
<212> TYPE: DNA
<213> ORGANISM: Artificial
<220> FEATURE:
<223> OTHER INFORMATION: Primer sequences

<400> SEQUENCE: 26
atactcgaga tgacctcctg ggctgtcctg ct                                32

<210> SEQ ID NO 27
<211> LENGTH: 30
<212> TYPE: DNA
<213> ORGANISM: Artificial
<220> FEATURE:
<223> OTHER INFORMATION: Primer sequence

<400> SEQUENCE: 27
cctagatctt caaatgaaac ctactggctt                                  30

<210> SEQ ID NO 28
<211> LENGTH: 14
<212> TYPE: PRT
<213> ORGANISM: Bos taurus

<400> SEQUENCE: 28

Met Thr Ser Trp Ala Val Leu Leu Ile Thr Ser Val Leu Leu
1               5                  10

<210> SEQ ID NO 29
<211> LENGTH: 25
<212> TYPE: DNA
<213> ORGANISM: Artificial

```
<220> FEATURE:
<223> OTHER INFORMATION: Primer sequence

<400> SEQUENCE: 29
atggacaagt tgggagatca gcccg                                              25

<210> SEQ ID NO 30
<211> LENGTH: 25
<212> TYPE: DNA
<213> ORGANISM: Artificial
<220> FEATURE:
<223> OTHER INFORMATION: Primer sequence

<400> SEQUENCE: 30
cccaggatgg ggtaagagga cccag                                              25
```

BOVINE LYMPHOCYTE-DERIVED ANTIBACTERIAL PROTEIN

FIELD OF THE INVENTION

The present invention pertains to the field of nucleic acid sequences that code for useful polypeptides and the polypeptides encoded by the nucleic acids. In particular, the present invention pertains to the field of nucleic acid sequences that encode polypeptides having anti-microbial activity and uses of such nucleic acid sequences to produce these proteins.

BACKGROUND OF THE INVENTION

Microbial infections, such as bacterial infections, that cause disease in people and in animals such as livestock and companion animals are of clear and obvious concern throughout the world. For example, bovine mastitis is the most important infectious disease affecting both the quality and quantity of milk produced in the world. This disease affects virtually every dairy farm and has been estimated to affect 38% of all cows. The disease can cause destruction of milk-synthesizing tissues which reduces milk production and alters milk composition. In severe cases, the productive performance of dairy cattle may be diminished permanently.

Thus, mastitis continues to be the single greatest impediment to profitable dairy production. Losses associated with mastitis cost American dairy producers about 2 billion dollars per year and cost dairy producers worldwide an estimated 25 billion dollars per year.

In spite of the severe economic impact of this disease on the dairy industry, the only widely accepted methods of mastitis control are based on post-milking teat disinfection and antibiotic therapy. These methods have the disadvantages that they are often ineffectual and result in milk loss during such treatments. Additionally, there is a growing concern in the United States and worldwide about the presence of drug residues in the food supply and the potential consequences for public safety.

There is a pressing need for an effective, safe, and economical mastitis treatment and prophylactic therapy which will reduce the dairy industry's dependence on chemical agents to attempt to prevent or treat mastitis.

The case of mastitis is only an example. In addition to mastitis, there are countless other microbial diseases, including bacterial diseases, of cattle and other animals, for which a therapy to reduce the incidence and/or to treat existing cases is needed.

It has been established through research that interleukin-2 (IL-2) stimulated porcine and human NK (natural killer) cells are capable of non-specific killing of bacteria which is mediated by the secretion of porcine NK-lysin and human granulysin, respectively. A parasitic protozoan, *Entamoeba histolytica*, also is capable of killing bacteria through the generation of a pore-forming protein called amoebophore.

Despite the considerable evolutionary distance between single-celled parasitic organisms and mammalian lymphocytes, the bacterial effector proteins porcine NK-lysin, human granulysin, and amoebophore are related members of the same saposin-like family of proteins, referred to as "SAPLIP"s. The SAPLIPs are small glycoproteins, often derived from larger precursor proteins in vivo, that carry out diverse functions through association with lipid membranes. The amino acid sequences of the SAPLIP family members include highly conserved cysteine residues that form disulfide bonds and provide a stable structure to the SAPLIPs. The SAPLIP members also share the characteristic that their secondary protein structure is made up mostly of α-helices joined by loops.

It has been demonstrated in in vitro studies that IL-2 stimulated bovine NK-cells possess antibacterial activity that is not MHC restricted. See, Sordillo, L M, et al., J. Dairy Sci., 74:3370 (1991), incorporated in its entirety herein by reference. This activity has been reported to be carried out by a small, secreted protein that is effective in small quantities and is not toxic to host cells. See, Sordillo-Gandy et al., International Patent Application Publication No. WO 98/08534 (1998), incorporated in its entirety herein by reference. This protein was reported to be approximately 16 kD in size as determined by SDS-PAGE and was shown to have antibacterial activity against a wide range of bacteria, including both gram-negative and gram-positive bacteria, without causing harm to host cells.

Although Sordillo-Gandy discloses the isolation of this protein, because it is produced in very small amounts by stimulated NK cells, the isolation of the protein in the native form is both tedious and time consuming. These difficulties have presented an impediment to further study of the protein and to utilizing the isolated native protein for its antimicrobial activity. Thus, a need exists for a means of obtaining this protein by a means other than by isolation.

BRIEF DESCRIPTION OF THE FIGURES

FIG. 1 shows 6 sets of forward and reverse gene specific primer (GSP) sets designed to amplify a putative bovine SAPLIP (bSAPLIP). Primers were designed using the SDSC Molecular Biology Workbench program and the TIGR database bovine cDNA sequence TC90773 as a template. Each of these primer sets was successful in amplifying the target sequence when used in RT-PCR with bovine CD2+/CD3− lymphocyte RNA. The forward primer labeled "Optimal" has been designated Seq. ID No. 1 and its corresponding reverse primer Seq. ID No. 2. The forward primer labeled "Product #1" has been designated Seq. ID No. 3 and its corresponding reverse primer Seq. ID No. 4. The forward primer labeled "Product #2" has been designated Seq. ID No. 5 and its corresponding reverse primer Seq. ID No. 6. The forward primer labeled "Product #4" has been designated Seq. ID No. 7 and its corresponding reverse primer Seq. ID No. 8. The forward primer labeled "Product #5" has been designated Seq. ID No. 9 and its corresponding reverse primer Seq. ID No. 10. The forward primer labeled "Product #6" has been designated Seq. ID No. 11 and its corresponding reverse primer Seq. ID No. 12.

FIG. 2 shows the putative 632 bp DNA sequence encoding bSAPLIP, designated Seq. ID No. 13, and the alignment of that sequence with TIGR sequence TC90773, designated Seq. ID No. 14. The 632 bp bSAPLIP sequence was derived from alignment of the resulting 5' and 3' RACE products as shown in FIG. 3. The TIGR sequence #TC90773 is located in The Institute for Genomic Research (TIGR) database, and was produced through alignment of mRNA clones (GenBank #'s AW325879, BE486646, AW658218). The TIGR sequence was used to develop primers for use in a RACE reaction using CD2+/CD3− bovine lymphocyte RNA. The RACE 632 bp putative bSAPLIP sequence was derived from alignment of the resulting 5' and 3' RACE products (see table 3 for RACE alignment). Regions of homology between the two sequences are underlined. The putative ORF for putative bSAPLIP is indicated by a dashed line. The last five lines of FIG. 2 is a continuation of the amino acid sequence of the TC90773 sequence.

FIG. 3 shows the alignment of 5' RACE clone (Seq. ID No. 15), shown in non-bolded text, and 3' RACE clone (Seq. ID No. 16), shown in bold text, generated with the GSPs shown in FIG. 1. A conserved region of 79 bp overlap was used for alignment and generation of a 632 bp full length sequence. The putative ORF of bSAPLIP is underlined. The putative start and stop codons are indicated by white text in a black box. The indicated ORF possesses 75% homology to the NK-lysin ORF(NCBI# X85431) and 61% homology to the granulysin ORF (NCBI # XM 002560).

FIG. 4 shows the alignment of the amino acid sequence of bSAPLIP (Seq. ID No. 17) with that of porcine NK-lysin (Seq. ID No. 18) and human granulysin (Seq. ID No. 19). Single, fully conserved residues are indicated with equal signs (=). Conserved strong groups are indicated with plus signs (+). Conserved weak groups are indicated with minus signs (-). Predicted hydrophobic leader sequences of granulysin and bSAPLIP are underlined.

FIG. 5 shows the alignment of the pre-proteins bSAPLIP (Seq. ID No. 20), NK-lysin (Seq. ID No. 21), and granulysin (Seq. ID No. 22) and proposed signal sequence cleavage sites. Single, fully conserved residues are underlined. Amino-terminal region of 100% homology between NK-lysin and bSAPLIP is in bold. Proposed signal sequence sites that are cleaved to produce the about 9 kD forms of NK-lysin, granulysin, and bSAPLIP are indicated with a caret (^).

FIG. 6 shows the cysteine to cysteine disulfide bridge formation for 9 kD bSAPLIP (Seq. ID No. 23). The proposed disulfide bridge formation pattern (1-6, 2-5, 3-4) between cysteine residues in the 9 kD bSAPLIP. The similar bond formation pattern for two SAPLIPs, 9 kD NK-lysin (Seq. ID No. 24) and 9 kD granulysin (Seq. ID No. 25), are shown for comparison. Conserved cysteine residues are indicated by bold and underlining. The granulysin bonding pattern is reported to have only two disulfide bridges, due in part to the post-translational cleavage of a carboxy-terminal sequence that contains a cysteine residue. This cleavage site is indicated with a caret (^).

FIG. 7 shows the hydrophobic regions and proposed α-helices of 9 kD bSAPLIP (Seq. ID No. 23) in comparison with those of NK-lysin (Seq. ID No. 24) and granulysin (Seq. ID No. 25). Positively charged arginine residues (R)are indicated by underlining. Conserved hydrophobic residues (V,I,L,P,A,W,M,F,Y) are indicated in gray boxes with dark lettering. the carboxy-terminal cleavage site of granulysin is indicated with a caret (^).

DETAILED DESCRIPTION OF THE INVENTION

According to one embodiment, the invention is a nucleic acid that encodes a polypeptide that has antibacterial activity, that is the polypeptide has bacteriocidal or bacteriostatic activity in vivo and/or in vitro. In a preferred embodiment, the nucleic acid is a deoxyribonucleic acid comprising the nucleotide sequence of Seq. ID No. 13. Alternatively, the nucleic acid is one that will hybridize under highly stringent hybridization conditions (at least 3×SSC, and preferably 6×SSC, at 65° C.) to the complement of nucleotide sequence of Seq. ID No. 13, which nucleic acid encodes a polypeptide having antibacterial activity.

In an alternative embodiment, the invention is a nucleic acid that encodes a polypeptide that has antibacterial activity, wherein, preferably, the nucleic acid is a deoxyribonucleic acid comprising Bases 198 to 452 of (encodes the 9 kD protein) the nucleotide sequence of Seq. ID No. 13. Alternatively, the nucleic acid is one that will hybridize under highly stringent hybridization conditions to the complement of Bases 198 to 452 of THE nucleotide sequence of Seq. ID No. 13 and which nucleic acid encodes a polypeptide having antibacterial activity.

In another embodiment, the invention is a polypeptide having antibacterial activity which is encoded by the nucleotide sequence of Seq. ID No. 13 or by a nucleic acid that will hybridize under highly stringent hybridization conditions to the complement of Seq. ID No. 13.

In another embodiment, the invention is a polypeptide having antibacterial activity and that is encoded by bases 198 to 452 of Seq. ID No. 13 or by a nucleic acid that will hybridize under highly stringent hybridization conditions to the complement of Bases 198 to 452 of Seq. ID No. 13.

In another embodiment, the invention is a method for making a polypeptide having antibacterial activity. According to this method, a host cell that is transformed with an expression vector that is integrated with a nucleic acid, such as a cDNA, comprising the nucleic acid sequence of Bases 198 to 452 of Seq. ID No. 13 or a nucleic acid sequence that will hybridize under highly stringent hybridization conditions to the complement of Bases 198 to 452 of Seq. ID No. 13 is caused to express the polypeptide encoded by the nucleic acid, and the expressed polypeptide is purified. If desired, but not necessarily, the nucleic acid comprises the entire sequence of Seq. ID No. 13 or is a nucleic acid sequence that will hybridize to the entire sequence of Seq. ID No. 13.

In another embodiment, the invention is an expression vector into which is integrated a nucleic acid sequence comprising Bases 198 to 452 of Seq. ID No. 13 or a nucleic acid sequence that will hybridize under highly stringent hybridization conditions to the complement of Bases 198 to 452 of Seq. ID No. 13. If desired, but not necessarily, the nucleic acid that is integrated into the expression vector may comprise the entire sequence of Seq. ID No. 13 or is a nucleic acid sequence that will hybridize to the entire sequence of Seq. ID No. 13.

In another embodiment, the invention is a host cell that is transformed with an expression vector into which is integrated a nucleic acid sequence comprising Bases 198 to 452 of Seq. ID No. 13 or a nucleic acid sequence that will hybridize under highly stringent hybridization conditions to the complement of Bases 198 to 452 of Seq. ID No. 13. If desired, but not necessarily, the nucleic acid that is integrated into the expression vector that is used to transform the host cell may comprise the entire sequence of Seq. ID No. 13 or is a nucleic acid sequence that will hybridize to the entire sequence of Seq. ID No. 13.

The nucleic acid of the invention may be a deoxyribonucleic acid or a ribonucleic acid. In a most preferred embodiment, the nucleic acid comprises the sequence of Bases 198 to 452 of Seq. ID No. 13. The nucleic acid of the invention may comprises the entire sequence of Seq. ID No. 13. Alternatively, the nucleic acid of the invention comprises a sequence of bases that will hybridize under highly stringent conditions to the complement of a nucleic acid having the sequence of Bases 198 to 452 of Seq. ID No. 13. The nucleic acid of the invention also encompasses those nucleic acids that contain conservative nucleotide changes from Seq. ID No. 13. It is understood in the art that deletions or additions to the amino or carboxy terminal portions of proteins may be made while retaining the activity of such proteins. Thus, the nucleic acid of the invention includes nucleic acids having a sequence of Bases 198 to 452 of Seq. ID No. 13 which lacks one or more bases 5' bases starting with base 198 and/or one or more 3' bases starting with base 452 or which includes additional bases beyond base no. 198 and/or base no. 452.

The RNA of the invention is complementary to the DNA of the invention, such as is described in the preceding paragraphs. That is, the RNA of the invention will hybridize to a DNA of Seq. ID No. 13, preferably to Bases 198 to 452 of SEQ. ID No. 13, or to a DNA that hybridizes under highly stringent conditions to a DNA that is complementary to the DNA of Seq. ID No. 13, and preferably to Bases 198 to 452 of SEQ. ID No. 13.

The polypeptide of the invention has antibacterial activity and is encoded by the nucleic acid of the invention. The polypeptide is conceived to be a member of the SAPLIP family of proteins and is encoded by a DNA sequence present in the bovine genome. In a preferred embodiment, the amino acid sequence of the polypeptide of the invention comprises that shown in Seq. ID No. 23. In another preferred embodiment, the amino acid sequence of the polypeptide of the invention comprises amino acids 4 to 76 of Seq. ID No. 23, that is it contains the six cysteines that are involved in disulfide bonding, as illustrated in FIG. 6. Generally speaking, a particular amino acid sequence (amino acids 4 to 76 of Seq. ID. NO. 23), or greater than about 70% sequence similarity and preferably greater than about 80% sequence similarity and most preferably greater than about 90% sequence similarity with that sequence, wherein the polypeptide having that sequence has antibacterial activity, characterizes the polypeptide of the invention.

The polypeptide, having the sequence of Seq. ID No. 23 has a molecular weight of about 9 kD, as determined by SDS-PAGE under denaturing conditions. In another preferred embodiment, the polypeptide comprises the amino acid sequence as shown in Seq. ID No. 20. The polypeptide, having the sequence of Seq. ID No. 20 has a molecular weight of about 10 kD, as determined by SDS-PAGE under denaturing conditions, which determined molecular weight is approximately the same as the 9 kD molecular weight of the polypeptide of Seq. ID No. 23. In another preferred embodiment, the polypeptide comprises the amino acid sequence as shown in Seq. ID No. 17. The polypeptide, having the sequence of Seq. ID No. 23 has a molecular weight of about 16 kD, as determined by SDS-PAGE under denaturing conditions.

The polypeptide of the invention also includes polypeptides having antibacterial activity that are encoded by the nucleic acids of the invention, as described above. Thus, a polypeptide that is encoded by Seq. ID No. 13, or by a nucleic acid comprising nucleotides 198 to 452 of Seq. ID No. 13, or by a nucleic acid that hybridizes under highly stringent hybridization conditions to all or a portion of Seq. ID No. 13 and which polypeptide has antibacterial activity, is included within the invention.

The polypeptide of the invention, as described in the preceding paragraph, may contain one or more conservative changes so long as the antibacterial activity of the polypeptide is retained. Accordingly, one or more amino acids may be added or deleted at either or both of the amino-terminal end or carboxy-terminal end. Also, amino acid substitutions may be made which maintain charge identity and steric configurations of the amino acid of the polypeptide. It is well understood in the art how to make such additions, deletions, or substitutions and that such changes may be made to a polypeptide while retaining the function of the polypeptide.

The polypeptide of the invention may be used as an antibacterial agent. For example, the polypeptide of the invention may be used in vitro, such as for killing bacteria associated with an inanimate object. The polypeptide may also be used to treat or to reduce the incidence of a bacterial infection, such as by topical application to the skin or to a mucosal surface, by injecting into a body cavity, such as by intramammary or intrauterine infusion, or by administering the polypeptide systemically, such as by subcutaneous, intramuscular, or intravascular injection. The route of administration and the effective dose of the polypeptide of the invention may vary depending on many factors, including site and route of administration.

The polypeptide may be used to produce antibodies, such as monoclonal or polyclonal antibodies, that specifically bind to the polypeptide. Such antibodies may be generated by known methods, such as those in Sambrook, et al., Molecular Cloning, A Laboratory Manual, Cold Spring Harbor Press. The antibodies may be used, for example, in isolation of the polypeptide and in diagnostic procedures for detection of the polypeptide.

The polypeptide of the invention may be expressed in prokaryotic or eukaryotic cells in accordance with known methods. For example, a unicellular organism, such as a bacterium like *E. coli*, or *Bacillus subtilis*, or yeast such like *Saccharomyces cerevisiae*, may be utilized. Alternatively, a multicellular organism or cells from a multicellular organism may be used to express the polypeptide. Examples include insect cells, such as in combination with baculovirus vectors, or cells of higher organisms such as plants, or animals such as vertebrates like mammals, for example COS 7 cells, and human cell lines.

Isolation or purification of the expressed polypeptide may be accomplished in accordance with conventional methods. A lysate may be prepared from the expression host and the lysate purified using HPLC, exclusion or affinity chromatography, gel electrophoresis or other purification technique. The purified polypeptide preferably is at least 80% pure, more preferably at least 90% pure, and most preferably about 100% pure. Pure, in this context, means free of other proteins and of cellular debris.

The following examples provide additional information how to make and to use preferred embodiments of the invention. The examples are not intended to limit the scope of what the inventor regards as the invention. The examples detail the inventor's search for bovine sequences that had homology with known SAPLIPs and confirmation that IL-2 stimulated production of the protein. Sequences obtained were utilized in a rapid amplification of cDNA ends (RACE) protocol which enabled a determination of the full length transcript of the bovine member of the SAPLIP family, the polypeptide of the invention.

EXAMPLE 1

Isolation of Mononuclear Cells

Peripheral blood mononuclear cells (PBMC) are collected to serve as sources of bovine lymphocyte RNA. PBMC are isolated from three mid-lactating Holstein dairy cows that are free of mastitis. Whole blood samples are centrifuged in 50 ml centrifuge tubes at 2000 RPM, 4° C. for 30 minutes. The interface layer is removed by pipetting, layered onto Ficoll-Paque (Amersham Pharmacia, Piscataway, N.J., USA), and centrifuged at 1370 RPM, 15° C. for 30 minutes. The buffy layer is removed by pipetting, placed in 20 ml Hank's balanced salt solution (HBSS, Sigma Aldrich, St. Louis, Mo., USA), and centrifuged at 1000 RPM, 10° C. for 10 minutes. Pellets are combined in HBSS. Remaining red blood cells are lysed with distilled and deionized water (ddH$_2$O), followed by addition of 2×RPMI (Roswell Park Memorial Institute medium) and HBSS. Tubes are centrifuged at 1000 RPM, 10° C. for 10 minutes, and pellets are combined and washed 3 times with HBSS containing 2% bovine serum albumin (BSA, Hyclone, Logan, Utah, USA). MØ are adhered out through flasking for 2 hours at 37° C. and the remaining cells are centrifuged at 1000 RPM, 10° C. for 10 minutes. Mononuclear cells are then resuspended in 5 ml HBSS. A 1:100 aliquot of cells is examined for viability through trypan blue exclusion and then counted using a hemocytometer.

EXAMPLE 2

Cell Separation Using Magnetic Beads

Enriched cultures of bovine NK-like lymphocytes (CD2+/CD3−) are obtained via magnetic bead separation. Isolated PBMC are incubated for 30 minutes with 200 µl of mouse anti-bovine CD3 (VMRD #MM1A, Pullman, Wash., USA) per 10$^7$ cells. The cells are then washed with 1X phosphate buffered saline (PBS)+2% BSA and incubated an additional 30 minutes at 4° C. with 10 µg of goat anti-mouse IgG coated magnetic beads (Miltenyi Biotech, Germany) per 10$^7$ cells. The bead cell complex is then extracted from non-complexed cells through the use of a magnetic field (Vairo-MACS Magnetic Separation Systems, Miltenyi Biotech, Germany) and the CD3− fraction is collected. The cells are counted and the process is repeated, this time labeling the cells with mouse anti-bovine CD2 (VMRD #BAQ95A, Pullman, Wash., USA). The CD2+/CD3− fraction, containing mainly NK-like cells, is then extracted in the manner previously described.

EXAMPLE 3

RNA Isolation

Cell cultures enriched for bovine NK-like lymphocytes are resuspended (10$^7$ cell/ml) in RPMI-1640 containing 10% fetal bovine serum (FBS, Hyclone, Logan, Utah, USA), 1% antibiotic/antimycotic solution (Sigma Aldrich, St. Louis, Mo., USA), and 1% L-glutaminutese (Sigma Aldrich). The cultures are then stimulated with 100 U/ml of recombinant human IL-2 (Roche Molecular, Mannheim, Germany) for 48 hours and 37° C. Control unstimulated cultures are also incubated for 48 hours at 37° C. After incubation, the cells are washed with HBSS and resuspended (5.0×10$^6$ cells/ml) in TRIZOL™ reagent (Invitrogen, Carlsbad, Calif., USA). Total RNA is isolated according to the manufacturer's instructions.

EXAMPLE 4

Generation of Bovine SAPLIP Partial Sequence

Primer sets are designed to determine if a sequence for a putative bovine SAPLIP could be isolated from IL-2 stimulated bovine NK-like lymphocytes. Gene specific primer (GSP) sets are designed using a bovine lymphocyte-derived sequence (TIGR database accession no. TC90773) with strong homology to porcine NK-lysin (NCBI#X85431). The sequences are aligned using the CLUSTALW alignment program. The primer sets are obtained from Gibco (Invitrogen, Carlsbad, Calif., USA).

Isolated RNA is converted to cDNA via reverse transcription (RT). The RT reaction is carried out in a final volume of 20 µl, using 1 µg of RNA, and contained 1 µM oligo (dT)-18 primer (Operon, Alameda, Calif., USA), 3 mM MgCl$_2$, 0.2 mM each of dNTPs, 1 U/µl of recombinant RNase inhibitor (Promega, Madison, Wis., USA), and 1 µM of recombinant murine leukemia virus reverse transcriptase (M-MLV, Promega). The reactions are incubated at 37° C. for 45 minutes, then subjected to 95° C. for 5 minutes to terminate the reaction. The resulting cDNA is used as a template in polymerase chain reactions (PCR) utilizing the designed GSPs.

The polymerase chain reactions using GSPs are carried out in a final volume of 50 µl that contained 3 mM MgCl$_2$, 0.2 mM each of dNTPs, 2.5 U of Taq polymerase (Promega, Madison, Wis., USA), and 30 pmol of forward and reverse primers from each GSP set (Invitrogen, Carlsbad, Calif., USA). The reactions are heated to 95° C. for a cycle of 3 minutes and then cycled 30 times through a 30 second denaturing step at 95° C., 30 second annealing step at 72° C., and 1 minute elongation step at 72° C. in a PTC-200 DNA Engine heated lid PCR thermocycler (MJ Research, Watertown, Mass., USA). Following the final cycle, an extension step at 72° C. for 5 minutes is included. The PCR products are visualized using a 1.5% NuSeive agarose gel stained with ethidium bromide. The product bands are then excised and purified using the QIAquick Gel Slice Purification kit (Qiagen, Valencia, Calif., USA) according to the manufacturer's instructions and ligated into pGEM T-Easy plasmid vector (Promega), transformed into competent DH5α *E. coli* (Invitrogen), and plated onto selection agar. Plasmids are purified from individual colonies using the WIZARD™ plasmid mini-prep system (Promega) and sequenced by the Nucleic Acid Facility at the Pennsylvania State University. The sequences obtained are aligned with the bovine SAPLIP homologue sequence using the CLUSTALW alignment program and compared to the GenBank database using BLAST (NCBI, Washington, D.C., USA).

Of ten GSP sets designed to amplify partial sequences of a putative bovine SAPLIP (bSAPLIP), all are successful in generating PCR fragments using CD2+/CD3− RNA as template. However, only six sets, shown in FIG. 1 and designated Seq. ID Nos. 1 to 12, are successful in generating single, distinct bands that proved to be the expected size (144 to 266 bp) when visualized through gel electrophoresis. The PCR products are cloned using pGEM T-Easy plasmid vector and sequence analysis is performed. CLUSTALW alignment of the cloned PCR products with the TIGR database putative bSAPLIP reveals a high degree of homology, indicating that the putative bSAPLIP mRNA is produced by bovine NK-like lymphocytes. A BLAST search on the cloned PCR products shows strong homology with SAPLIP family members porcine NK-lysin (pNK-lysin) and human granulysin (hGranulysin). These results indicate that, when bovine NK-like lymphocyte RNA is used as a template, the designed GSPs can amplify a putative bSAPLIP with homology to other SAPLIP family members.

EXAMPLE 5

Rapid Amplification of cDNA Ends (RACE)

Whole bovine RNA isolated from IL-2 stimulated and unstimulated NK-like lymphocytes is used as template for the GeneRacer RACE kit (Invitrogen). Used according to the manufacturer's instructions, the GeneRacer kit facilitates the enzymatically assisted degradation of contaminating RNA in the samples while selecting for full length, capped mRNAs. Both 5' and 3' RACE-ready cDNAs are generated by converting 1 µg of the full length mRNAs to cDNA via a first strand cDNA synthesis reaction. A positive control for the generation of the 5' and 3' RACE-ready cDNA populations is performed using control (HeLa) RNA provided with the kit. First strand synthesis reactions (total volume=20 μl) are incubated at 85° C. for 15 minutes to inactivate the MMLV-RT and then stored at −20° C. until use.

The RACE-ready mRNAs are utilized in 5' and 3' reactions. The 5' RACE product is generated using the indicated PCR mix, the GeneRacer 5' universal primer and the bovine SAPLIP "reverse primer 7/5". This GSP is designed using the TIGR database sequence for a bovine SAPLIP homologue and PrimerSelect software (Dnastar, Madison, Wis., USA). The 3' RACE product is generated by using the indicated PCR mix, the GeneRacer 3' universal primer and the bovine SAPLIP "forward primer 9". This gene specific primer is also designed using the bovine SAPLIP homologue sequence and PrimerSelect software. Reactions are heated to 94° C. for 2 minutes and then cycled 3 times through a 30 second denaturing step at 94° C. for 2 minutes and a 3 minute annealing step at 72° C.; cycled 10 times through a 30 second step at 94° C., a 30 second step at 70° C., and a 3 minutes step at 72° C.; cycled 20 times through a 30 second step at 94° C., a 30 second step at 68° C., and a 3 minute step at 72° C.; and cycled once through a 10 minute step at 72° C. using a PTC-200 DNA Engine (MJ Research, Watertown, Mass., USA). The resulting products are then visualized using a 1.5% NuSeive agarose gel stained with ethidium bromide.

Both the 5' and 3' RACE products are ligated into pGEM T-Easy plasmid vector (Promega) according to the manufacturer's instructions, transformed into competent DH5α *E. coli* (Invitrogen), and plated onto selection agar. Plasmids are purified from individual colonies using the WIZARD™ plasmid mini-prep (Promega) and sequenced by the Nucleic Acid Facility at the Pennsylvania State University. The sequences obtained are aligned with the bovine SAPLIP homologue sequence using the CLUSTALW alignment program and compared to the GenBank database using BLAST (NCBI, Washington, D.C., USA). The secondary structure of the protein is predicted using the Predict Protein Server.

The proposed full length ORF for putative bSAPLIP is generated using the 3' and 5' RACE reaction in conjunction with the GSPs previously tested. The 3' and 5' RACE reactions yield products of 392 bp and 319 bp, respectively, with no amplification of extraneous product. The RACE products are cloned into PGEM T-Easy vector and sequence analysis is performed. CLUSTALW alignment of the sequences reveals that the 3' and 5' RACE products (Seq. ID Nos. 16 and 15, respectively) overlap with a portion of the putative bSAPLIP sequence (Seq. ID No. 14) from the TIGR database, as shown in FIG. 2. When aligned with each other, the 3' and 5' RACE products overlap for a sequence of 79 base pairs, as shown in FIG. 3. Further sequence analysis yields a full length sequence of 632 bp (Seq. ID No. 13) with an ORF for putative bSAPLIP of 441 bp that contains both start and stop codons.

EXAMPLE 6

Putative Bovine SAPLIP ORF Homology to known SAPLIPs

A nucleotide BLAST search shows that the ORF for putative bSAPLIP has significant homology to both pNK-lysin mRNA (NCBI #X85431) and hgranulysin mRNA (NCBI #XM002560). SAPLIP family members often have more homology at the protein level than at the ORF level. Therefore, the ORF is translated to produce a 147 residue polypeptide and is tested to determine homology to known SAPLIPs through BLAST and sequence alignment.

As shown in FIG. 4, a BLAST search yields proteins with homology to the translated bSAPLIP ORF (Seq. ID No. 17), including pNK-lysin (NCBI #CAA59720) (Seq. ID No. 18) and hGranulysin (NCBI #XP 002560) (Seq. ID No. 19). CLUSTALW alignment shows that the putative ORF shares 60% homology with pNK-lysin and 37% with hgranulysin. The full length bSAPLIF protein from the bSAPLIF ORF is predicted to have a molecular weight of 16 kD, while the predicted molecular weight of pNK-lysin is 13.4 kD and that of hgranulysin is 15 kD. The active forms of these SAPLIPs are the products of post-translational cleavage of larger proteins, as shown in FIG. 5. In both pNK-lysin and hGranulysin, the cleaved form contains a SAPLIP region that is defined by the presence of conserved residues. Importantly, a homologous SAPLIP region is present in the carboxy terminal portion of the bSAPLIP protein. The SAPLIP region of the bovine protein is predicted to have a molecular weight of about 9 kD (9.4 kD) in comparison to 9.35 kD for pNK-lysin and 9.5 kD for hGranulysin. This is indicated by the presence of six cysteines that are positionally conserved among SAPLIP family members, as shown in FIG. 6.

Conceptual translation of this SAPLIP region of the bovine 9.4 kD ORF using the PredictProtein server reveals important secondary structural homology between the protein of the invention and other SAPLIPs. The translated SAPLIP region of the bovine sequence displays considerable conservation of the amino acids that are implicated in helix formation in pNK-lysin, as shown in FIG. 7. The putative bSAPLIP is predicted to be 69.0% alpha helices (α-helices), and defined as having an "all α-helix" formation. In comparison, pNK-lysin and hGranulysin also are predicted to be "all α-helix", with 75.9% and 69.9% α-helices, respectively. The PredictProtein GLOBE program defines putative bSAPLIP, as well as pNK-lysin and hGranulysin, as having compact globular protein conformations.

EXAMPLE 7

Cloning of Bovine SAPLIP into a Baculovirus Transfer Vector

Putative open reading frames (ORF) for bovine SAPLIP are determined using EditSeq software (Dnastar) and directionally cloned into a pBacPAK8 baculovirus transfer vector (Clontech, Palo Alto, Calif., USA). The ORF with homology to a known SAPLIP family member, porcine NK-lysin, is identified through comparison of the ORF to the GenBank database using BLAST. The ORF is amplified from RNA collected form IL-2 stimulated bovine NK-like cells (CD2+/CD3−), using GSPs developed using PrimerSelect software (Dnastar). The GSPs (Operon, Alameda, Calif., USA) incorporate sequences designed to add XhoI and BglII restriction sites to 5' and 3' ends of the amplified ORF, respectively, and these sites facilitate directional cloning of the product into the pBacPAK8 baculovirus transfer vector. Isolated RNA is converted to cDNA via RT, as described above. The resulting cDNA is used as template for a PCR reaction using the GSPs. The PCR reaction using the GSPs is carried out in a final volume of 20 μl that contained 3 mM $MgCl_2$, 0.2 mM each of the dNTPs, 2.5 U of Taq polymerase (Promega), and 30 pmol each of GSP "ORF fwd #3" (5'-ATACTCGAGAT-GACCTCCTGGGCTGTCCTGCT-3') (Seq. ID No. 26) and GSP "ORF rev #3" (5'-CCTAGATCTTCAAATGAAAC- CTACTGGCTT-3') (Seq. ID No. 27). The reactions are heated to 95° C. for a cycle of 3 minutes, and then cycled 25 times through a 30 second denaturing step at 95° C., 30 second annealing step at 65° C., and 1 minute elongation step at 72° C. in a PTC-200 DNA Engine heated lid PCR thermocycler (MJ Research). A sample of 5 µl of the PCR product is visualized using a 1.5% NuSeive agarose gel stained with ethidium bromide. The PCR products are ligated into the pBacPAK8 baculovirus transfer vector using T4 DNA Ligase (Promega) according to the manufacturer's instructions, transformed into competent DH5α E. coli and plated onto selection agar. Plasmids are purified from individual colonies using the WIZARD™ plasmid mini-prep. Clones are checked for insert through a double digest with XhoI and BglII restriction enzymes (Promega), then visualized using a 1.5% NuSeive agarose gel stained with ethidium bromide. Positive clones are sequenced at Davis Sequencing using BAC1/BAC2 sequencing primers (Clontech), and aligned with the putative bovine SAPLIP sequence using the CLUSTALW alignment program.

A double digest of the vector yields the amplified ORF of bSAPLIP and sequencing, using the BAC1/BAC2 sequencing primers reveals that the ORF is inserted into the transfer vector in the correct orientation.

EXAMPLE 8

Recombinant Baculovirus Production

The recombinant pBacPAK8 transfer vector, generated as described above, is used as part of a cotransfection to infect a population of Sf21 insect cells for the purpose of making a stock of recombinant baculovirus. Plasmids are purified from 10 ml bacterial culture using the WIZARD™ plasmid mini-prep. Grace's complete/basic medium (GibcoBRL #11605-094) is substituted for BacPAK complete/basic medium, allowed by the protocol. The remaining protocol is carried out according to the manufacturer's instructions.

EXAMPLE 9

Recombinant Production of Bovine SAPLIP

Supernatants are collected from the Sf21 insect cells that are infected with the recombinant baculovirus, and the remaining cells are scraped into sterile tubes with Grace's complete medium to which no gentamicin had been added (GibcoBRL, #11605-094). These cells are sonicated 4 times for 15 seconds each time using a water bath sonicator, then spun at 1000 g, 4° C. for 5 minutes, and the supernatants collected in sterile tubes followed by storage at 4° C. The previously collected supernatants are then combined with their respective cell lysates. Sf21 culture flask (25 cm$^2$) monolayers, seeded the night before at a density of $1.5 \times 10^6$ cells, are then experimentally infected with the collected supernatants in 5 ml Grace's complete medium to which no gentamicin had been added. The remaining protocol and controls are carried out according to the manufacturer's instructions. The flasks are left to incubate for 48 hours at 27° C., at which time the supernatants are collected, spun at 1000 g, 4° C. for 5 minutes, and stored at 4° C. in sterile tubes.

EXAMPLE 10

Bacterial Assay Using Experimental Cell Free Supernatants

The supernatants containing the recombinant protein are tested for bactericidal activity against Neubold *Staphylococcus aureus*. Three colonies of *S. aureus*, isolated from a fresh streak plate, are used to inoculate a 100 ml bottle of sterile UHT 2% fat milk (Parmalat). The culture is then incubated at 37° C. for 6 hours on a rotor. A series of ten-fold serial dilutions of this culture are then made using sterile 1×HBSS. 100 µl each of the $10^{-6}$, $10^{-7}$, and $10^{-8}$ dilutions are plated on blood agar (Remel, Lenexa, Kans., USA), in triplicate and incubated overnight at 37° C. The dilutions are stored at 4° C. The dilution used in the bactericidal assay is selected based on the number and spacing of bacterial colonies observed with a count of roughly $5.4 \times 10^2$ cfu/ml deemed optimal. The cell-free supernatants containing recombinant protein are combined with the selected *S. aureus* dilution in a sterile centrifuge tube at a ratio of 100 µl supernatant:900 µl *S. aureus* dilution. These samples are then incubated for 30 minutes at 37° C. with agitation. From each of these samples, 100 µl is placed in triplicate on blood agar, which is then left to incubate overnight. Decreases are observed decreases in the cfu/ml count, as compared to controls, which are attributed to bactericidal activity.

As shown in the above examples, the TIGR database of bovine cDNAs was searched for a bovine homologue to pNK-lysin, which search resulted in a 1157 bp cDNA (# TC90773) with strong homology to both hGranulysin and pNK-lysin. Additionally, this sequence was originally isolated from bovine lymphoid tissue, indicating that the cellular source could be the same as that for the antibacterial protein which is secreted by NK-like lymphocytes that was disclosed in Sordillo-Gandy, WO 98/08534. The TC 90773 sequence was used as a template for the generation of putative bSAPLIP PCR primers. Ten sets of primers were developed, each of which was successful in generating product when used in an RT=PCR with bovine CD2+/CD3− (NK-like lymphocyte) RNA. Five of the GSP sets amplified a single, distinct band of product, varying between 144 and 266 bp in length which is the expected size in relation to the primer placement on the putative bSAPLIP from the TIGR database. Cloning and subsequent sequencing revealed that the amplified products were 100% homologous to a portion of the sequence from the TIGR database. The sum of these observations indicates that mRNA for a putative bSAPLIP is produced within the effector cell population, mainly NK-like bovine lymphocytes, responsible for secretion of the antibacterial polypeptide.

The GSPs that amplified putative bSAPLIP were subsequently used as primers in both 5' and 3' RACE reactions. When aligned using CLUSTALW, the GSP "FWD 9" 3' RACE product having the sequence 5'-ATGGACAAGT-TGGGAGATCAGCCCG (Seq. ID No. 29) and the GSP "REV OPTIMAL" 5' RACE product having the sequence 5'-CCCAGGATGGGGTAAGAGGACCCAG (Seq. ID No. 30) displayed a considerable overlap of 79 base pairs. The alignment yielded a putative full-length bSAPLIP cDNA sequence of 632 bp, including a polyadenosine tail region of 22 bp.

Overall this cDNA is somewhat smaller than the cDNAs of pNK-lysin (780 bp) and hgranulysin (738 bp). It is noted, however, that the alignment of the above RACE products resulted in a cDNA with only 12 bp of sequence 5' of the putative start codon, while pNK-lysin and hGranulysin have 195 bp and 128 bp, respectively 5' of their start codons. In spite of these differences in length, the derived nucleotide sequence of putative bSAPLIP is 68% homologous to pNK-lysin (NCBI # X85431) and 62% homologous to hGranulysin (NCBI # XM002560). An ORF of 441 bp that contains a methionine start codon was detected within this sequence. The ORF for hGranulysin also contains a methionine start codon, while the sequence for pNK-lysin has a putative methionine start codon sequence upstream of the ORF. Importantly, it should be noted that the length of the ORF for putative bSAPLIP, 441 bp, is quite comparable to that of the ORFs for pNK-lysin (416 bp) and hGranulysin (393 bp). Furthermore, the putative bSAPLIP ORF possesses 75% homology to the pNK-lysin ORF and 61% homology to the hGranulysin ORF. These data indicate that the full length ORF for bovine SAPLIP has been isolated.

Translational analysis confirmed that the amino acid sequence of the bSAPLIP protein displays defining characteristics of the SAPLIP family. Many SAPLIPs, including both hGranulysin and pNK-lysin, exist in vivo in a number of forms that are differentiated by post-translational modifications. hGranulysin originates as a large pre-protein form, which is then modified to produce a 15 kD protein, which is again cleaved to generate the active 9 kD form of hGranulysin. The putative bSAPLIP ORF has an amino-terminal sequence of 14 amino acids, (5'-MTSWAVLLITSVLL-3') (Seq. ID No. 28), that shares conservation of strong groups and 50% homology with a predicted leader sequence in pre-protein hGranulysin. In the available sequence for pNK-lysin, this leader sequence is absent, but in hgranulysin, this sequence is believed to be cleaved to produce the 15 kD form of the protein. When the homologous leader sequence is conceptionally cleaved in a similar manner from the putative bSAPLIP protein, a 16 kD form of the protein is produced.

A BLAST search of this 16 kD bovine protein indicates that both pNk-lysin (NCBI #CAA59720) and hGranulysin (NCBI # XP 002560) share considerable homology. CLUSTALW alignment shows a 60% homology between putative bSAPLIP and pNK-lysin, with conservation of a number of individual residues, while a homology of 37% is observed between 15 kD hgranulysin and putative bSAPLIP. Interestingly, a sequence of 11 amino acid located at the amino-terminal end of the bovine protein shares 100% homology with pNK-lysin and 72% homology with hGranulysin, suggesting a conserved role for the sequence in cellular processing or protein function. Although the amino acid sequence of other portions of the bSAPLIP polypeptide differ significantly from those of NK-lysin and granulysin, the presence of the amino-terminal conserved region is a further indication that the polypeptide of the present invention is a member of the SAPLIP family.

SAPLIPs often undergo post-translational cleavage events that generate active proteins from pre-proteins, and the 15 and 13.4 kD pre-protein forms of hgranulysin and pNK-lysin, respectively, are subject to cleavage events in vivo that result in the generation of smaller, long-lived peptides with antibacterial activity. The pre-protein forms contain partially conserved sequences of residues that signal cleavage events and, post-cleavage, these residues will comprise the amino-terminal portion of the 9 kD active peptides. The putative bSAPLIP protein appears to contain such a cleavage sequence (see FIG. 5) when aligned with hGranulysin and pNK-lysin. hGranulysin and pNK-lysin also are believe to undergo a carboxy-terminal modification in the generation of active proteins from pre-proteins. A carboxy-terminal sequence located in the bovine sequence has some homology with C-terminal ends that are removed in this modification in the SAPLIPs (see FIG. 6), suggesting that the bSAPLIP of the invention also undergoes such modification.

The end result of the cleavage events and post-translational modifications is the generation of stable, mature, roughly 9 kD forms of the SAPLIPs hGranulysin and pNK-lysin. Within their carboxy-terminal regions are the cysteines and hydrophobic residues that define the SAPLIP domain, a conserved pattern detected throughout the SAPLIP family of proteins. These cysteine residues generate disulfide bridges that are important for SAPLIP secondary structure and function. In hgranulysin, reduction of these bonds results in a decrease, but not abolition, of killing activity, while in pNK-lysin, bond reduction with DTT causes a complete loss of function. When the putative bSAPLIP amino acid sequence is aligned with 9 kD hgranulysin and pNK-lysin, this conserved SAPLIP region is evident. The putative 9.4 kD form of bovine SAPLIP contains six cysteine residues that have 100% conserved alignment with the six cysteine residues in pNK-lysin, and therefore the proposed order of cysteine disulfide bridge formation for putative bSAPLIP is the same as that for pNK-lysin (See FIG. 6). Five of the putative bSAPLIP cysteine residues align with residues of hGranulysin, while the sixth aligns with a hgranulysin tyrosine (Y) residue. While the possible significance of this residue in hgranulysin is not known, it is noted that the nucleotide difference between tyrosine and cysteine is limited to only one base pair.

The conserved amino acid residues present in the SAPLIPs pNK-lysin and hGranulysin result in secondary protein conformations rich in α-helices, connected by loop regions and stabilized by disulfide bridges. The α-helices are amphipathic in nature as a result of both hydrophobic and hydrophilic residues. The combination of disulfide bridges and amphipathic regions results in a globular protein that is very compact and exhibits a characteristic "SAPLIP fold", with hydrophilic outer residues and hydrophobic inner residues. Using the PredictProtein server, the structure of the 9.4 kD form of putative bSAPLIP, the 9.35 kD form of pNK-lysin, and the 9.5 kD form of hGranulysin were characterized. PNK-lysin was defined as having 75.9% α-helices and 24.1% loop regions, a conformation that was termed "all-alpha" by the program. HGranulysin was defined as having 69.9% α-helices and 30.1% loop regions, and was also defined as "all-alpha". The putative bSAPLIP protein of the invention was defined as having 60.9% α-helices and 30.9% loop regions, scores considerably close to those found for the SAPLIPs and all resulting in an "all-alpha" designation for this protein. In addition, all three proteins were predicted to have a compact globular conformation, which is in agreement with previous characterization of SAPLIP family members.

The relative importance of α-helices for the functioning of pNK-lysin and hgranulysin has been established. Recombinant hgranulysin peptides that represent helix-loop-helix regions were found to exhibit strong bactericidal activity against E. coli and Mycoplasma tuberculosis, while regions without helices lacked activity. Subsequent destruction of positively charged arginine (R) residues within the α-helices resulted in both greatly reduced binding, of the proteins to E. coli and M. tuberculosis and abrogation of killing. This indicates that the specific interaction of positively charged SAPLIP residues with the negatively charged target cell phospholipid membrane is likely of considerable importance for killing activity Positively charged surface residues in pNK-lysin also have been implicated in a suggested mechanism of SAPLIP killing activity; molecular electroporation. Through this mechanism, transient binding of a cationic, α-helical protein with a negatively charged phospholipid membrane generates an electrical field that destabilizes the membrane, resulting in osmotic lysis. This membrane could explain the broadspectrum killing activity exhibited by SAPLIPs that seems to result from a transient disruption of target cell membranes without traditional pore formation. The Protein Calculator program was used to determine the charge at pH 7.00 of the 9 kD forms of pNK-lysin, hGranulysin, and the bSAPLIP of the invention. pNK-lysin had a predicted charge of 8.7, hGranulysin a charge of 10.8, and bSAPLIP a charge of 8.0. These results confirm the overall cationic character of each protein that is believe to result from the positive residues observed in their amino acid sequences. The cationic charge of bSAPLIP is comparable to those of pNK-lysin and hGranulysin and may further implicate molecular electroporation as a possible mechanism for bSAPLIP's bactericidal activity.

The presence of hydrophobic residues, along with disulfide bonds, is intrinsic to the formation of the characteristic "SAPLIP fold" of the 9 kD SAPLIP proteins. Indeed, alignment of pNK-lysin and hgranulysin proteins reveals conserved regions of hydrophobic residues (V,I,L,P,A,W,M, F,Y). Importantly, when the bovine protein is aligned with these known SAPLIPs, these hydrophobic regions are also conserved (See FIG. 7). Together with the predicted α-helical percentages of the bSAPLIP, these results indicate that the polypeptide of the invention also likely possesses the SAPLIP fold, which is characteristic of the SAPLIP family of proteins.

The bSAPLIP sequence displays considerable homology with known SAPLIPs at both the nucleotide and protein levels. When aligned with pNK-lysin and hGranulysin, the bovine protein exhibits conserved cysteine residues that are responsible for the disulfide bonds that contribute to the stability, protein conformation, and killing activity of SAPLIPs. The bovine protein also shares a motif of hydrophobic residues that contribute to the generation of amphipathic α-helices and, presumably, a characteristic SAPLIP fold. These finding indicate that the nucleotide sequence of the invention, when translated, produces a polypeptide that is compact, rich in amphipathic α-helices, and cationic. The findings indicate that the novel polypeptide of the invention referred to herein as bovine SAPLIP, is encoded by the nucleotide sequence of the invention.

The present invention has been described in terms of particular embodiments proposed to comprise preferred modes for the practice of the invention. It will be appreciated by those skilled in the art that, in light of the above disclosure, numerous modifications and changes may be made in the particular embodiments described and exemplified without departing from the scope of the invention. For example, due to codon redundancy, changes may be made in the sequence of nucleic acids without affecting the polypeptides encoded thereby. Moreover, changes may be made in protein structure, such as additions, deletions, and substitutions of amino acids as described above, with minimal or no affect on the activity of the protein. Such modifications and changes are intended to be included within the scope of the following claims.

The invention claimed is:

1. An isolated deoxyribonucleic acid (DNA) comprising the nucleotide sequence of bases 198 to 452 of Seq. ID No. 13 or a DNA that hybridizes under highly stringent conditions of at least 3×SCC at 65° C. to the complement of the nucleic acid comprising the nucleotide sequences of bases 198 to 452 of Seq. ID No. 13, wherein the DNA encodes a polypeptide of about 16 kD when measured by SDS PAGE under denaturing conditions, which polypeptide has has antibacterial activity.

2. An isolated ribonucleic acid that is fully complementary to the DNA of claim 1.

3. An expression vector into which is integrated the DNA of claim 1.

4. A host cell that is transformed with an expression vector into which is integrated the DNA of claim 1.

5. An isolated deoxyribonucleic acid (DNA) comprising the nucleotide sequence of bases 198 to 452 of Seq. ID No. 13, which DNA encodes a polypeptide that has antibacterial activity.

6. An isolated ribonucleic acid that is fully complementary to the DNA of claim 5.

7. An isolated deoxyribonucleic acid (DNA) comprising the nucleotide sequence of bases 13 to 453 of Seq. ID No. 13.

8. The isolated DNA of claim 7 which comprises the nucleotide sequence of bases 1 to 632 of Seq. ID No. 13.

* * * * *

UNITED STATES PATENT AND TRADEMARK OFFICE
CERTIFICATE OF CORRECTION

PATENT NO. : 7,160,696 B2  
APPLICATION NO. : 10/413600  
DATED : January 9, 2007  
INVENTOR(S) : Lorraine Sordillo It is certified that error appears in the above-identified patent and that said Letters Patent is hereby corrected as shown below:

Col 1, Line 5 insert
--This invention was made with government support under Grant No. 98-34163-6012 awarded by the USDA. The Government has certain rights in the invention.--

Signed and Sealed this

Second Day of September, 2008

JON W. DUDAS  
*Director of the United States Patent and Trademark Office*